United States Patent [19]
Murnick et al.

[11] Patent Number: 5,361,772
[45] Date of Patent: Nov. 8, 1994

[54] BREATH COLLECTION DEVICES

[75] Inventors: Janet G. Murnick, Bernardsville; Richard A. Cronenberg, Mahwah, both of N.J.

[73] Assignee: Diagnostics & Devices, Inc., Bernardsville, N.J.

[21] Appl. No.: 88,157

[22] Filed: Jul. 7, 1993

[51] Int. Cl.5 .......................................... A61B 5/097
[52] U.S. Cl. .................................................... 128/730
[58] Field of Search ....................... 128/716, 719, 730; 73/23.3, 863.73, 863.81, 863.85

[56] References Cited

U.S. PATENT DOCUMENTS

| | | | |
|---|---|---|---|
| 3,858,573 | 1/1975 | Ryan et al. | 128/730 |
| 4,067,320 | 1/1978 | Olsson et al. | |
| 4,617,821 | 10/1986 | Yokoyama et al. | |
| 4,947,861 | 8/1990 | Hamilton | |
| 5,052,213 | 10/1991 | Stock | |
| 5,111,827 | 5/1992 | Rantala | |
| 5,140,993 | 8/1992 | Opekun, Jr. et al. | |
| 5,193,551 | 3/1993 | Pilipski | 128/716 |

OTHER PUBLICATIONS

Michael Phillips, "Breath Tests in Medicine", Jul. 1992 issue of Scientific American.
Brochure, "Your Guide to the $^{13}$C-Urea Breath Test", Martek Diagnostics.
Brochure, "Conducting the Urea Breath Test", Metabolic Solutions, Inc.

Primary Examiner—William E. Kamm
Assistant Examiner—Brian M. Green
Attorney, Agent, or Firm—Lerner, David, Littenberg, Krumholz & Mentlik

[57] ABSTRACT

A breath sampling device has a body defining an interior space or bore with two open ends. The patient's breath is directed through the device from end to end, thereby continually purging the interior space. At a designated time during the breath, closure devices are actuated to shut both ends, desirably in response to a single actuation movement, thereby capturing a breath sample at a predetermined time. The continual purging action assures that the captured breath sample truly represents the breath at the designated time during the exhalation cycle.

18 Claims, 4 Drawing Sheets

BREATH COLLECTION DEVICES

FIELD OF THE INVENTION

The instant invention relates to methods and apparatus for the selective segregation and retention of a sample of expired breath from a stream of expired breath.

BACKGROUND OF THE INVENTION

Breath testing has been used in medicine since ancient times.

There have been considerable improvements in tests which can be applied to breath samples for diagnostic purposes. These improvements have prompted renewed efforts to develop breath sample collection devices and methods. A breath sample collection device must meet several conflicting requirements. To avoid the possible infection risks associated with reusable devices, the sample collection device should be disposable. Therefore, the device should be manufacturable at low cost. However, the device should provide for secure capture of a breath sample which truly represents the content of the breath stream at, a particular time during exhalation. The air expelled by a patient during exhalation varies in composition. The first air expelled consists essentially of air disposed in the mouth, nose and upper respiratory tract. Air expelled at a later time during the same exhalation will consist essentially of air from the bronchi and lower respiratory tract, whereas the last air expelled will consist essentially of air from the alveolar or air sacks of the lungs themselves. It is desirable to capture a particular portion of the exhaled air to provide a test sample which truly represents one portion, and one portion only, of the breath. For example, in metabolic testing it is generally desirable to capture alveolar air, and to exclude other portions of the exhaled air. Thus, the sampling device should be capable of selectively capturing a desired portion of the breath stream without substantial contamination by other portions of the breath stream. The device must also provide for secure storage of the captured sample until the same can be transferred to an analytical instrument. The device should be simple to use, both in capturing the sample and in transferring the sample to an analytical instrument. All of these requirements, taken together, have posed considerable technical challenge heretofore.

One device which has been proposed uses a plastic bag with attached mouthpiece into which the patient expels an expired breath stream. While the expired breath is still being expelled, a syringe is used to draw off a sample. Once the sample is collected, a stopcock on the syringe is closed and a needle is affixed to the end of the syringe. A portion of the sample is then placed in a test tube by using the needle to pierce the sealing membrane of an evacuated test tube. The sample captured in the bag will be a mixture of all portions of the exhaled breath, including air present in the lungs, respiratory tract and the mouth. The sample therefore will not accurately represent any particular portion of the exhaled breath. Another device using a flexible bag is described in U.S. Pat. No. 5,140,993, and suffers from similar drawbacks.

Another device uses a test tube-like sample container which has a permanently closed bottom end and an open top end or mouth. A membrane with two crossed slits is fixed at the mouth of the container.

The user inserts a straw through the cross-slits of the membrane, so that an open end of the straw is disposed adjacent to the bottom end of the container. The user then blows through the straw, forcing breath through the container and out of the mouth of the container by way of the slits in the membrane. To terminate the sample, the user must pull the straw out of the container. It is not possible to seal out extraneous air from outside the container during the test. The straw does not provide for complete purging of the container. There is some mixing of the breath entering with the air in the container. While the straw is being withdrawn, the air at the bottom of the container remains undisturbed. Thus, the sample left in the container will be contaminated with air from undesired parts of the exhalation cycle. Also, as the straw is withdrawn so that the sealing cap can be applied, there is a chance of losing a portion of the sample or mixing it with air from outside the tube. Apparently, this technique is not too successful since the instructions state, "if you are not sure the procedure was done correctly, relax and do it again in the same tube." To reuse the tube under these conditions could only make the sample more suspect.

Another breath-collection device is shown and described in an article entitled, "Breath Tests in Medicine" by Michael Phillips in the July 1992 issue of Scientific American. This device is highly complex and extremely large and must be mounted upon a cart, making its usefulness limited. The Phillips device employs activated carbon filters, water traps, breath traps, pumps and many complex interconnections. The size and complexity of the device limits its use to hospitals, clinics, etc.

U.S. Pat. No. 5,052,213 illustrates a device in which a recess in a slide is positionable within a housing to act first during the gas collection as a part of the flow duct for the exhalation of air and then to act as a part of the detector during a test cycle wherein the content of the recess is directed to the detector. Thus, for at least a short period of time a sample of the exhaled air is retained in the recess and is later subject to analysis. There is no provision for removing the sample from the recess for analysis by anything other than the associated device.

U.S. Pat. No. 4,617,821 shows a free standing gas detection device which includes both the collection and analysis of a breath sample in one unit. U.S. Pat. No. 5,111,827 shows a combined device which contains both a sampling connector for a gas analyzer and spirometer. U.S. Pat. No. 4,067,320, provides a drift compensation system for a gas analyzer. No effort is made to seal a sample of gas or breath in a batch device for later analysis in an independent analyzer.

Despite all of these efforts in the art, however, there have still been acute needs for improvements in breath sampling devices and methods.

SUMMARY OF THE INVENTION

One aspect of the present invention provides a device for capturing and retaining a sample of expired breath from an exhaled breath stream. A device according to this aspect of the invention may include body means for defining an interior space, and first and second openings on opposite sides of the interior space. Thus, a stream of breath may be directed into the interior space through the first opening, and out of the interior space through the second opening. The device may further include valve means for stopping communication between the space and the exterior through both of the openings to thereby interrupt the stream of breath and trap a sample of the stream in the interior space. Additionally, the device may include access means for selectively providing access to the interior space after capture of the breath sample so as so permit withdrawal of a portion of the trapped sample at a time after the sample has been collected. Most preferably, the interior space is substantially in the form of an elongated bore having a lengthwise dimension, in the direction along the length of the bore between the ends thereof, substantially greater than the dimensions of the bore transverse to the lengthwise direction. The first and second openings desirably are disposed adjacent to the ends of the interior space or bore. Thus, while the patient is exhaling through the device, prior to closure of the valve means, substantially all of the volume within the interior space or bore is continually being purged by freshly-exhaled breath. The sample captured when the valve means are closed is a substantially pure, uncontaminated sample of the breath being exhaled at the time of closure. Most preferably, the valve means are arranged to close both openings in response to a single actuation movement.

A particularly preferred device in accordance with present invention may include a body defining an interior space having first and second ends, the interior space preferably being in the form of an elongated bore having opposite ends. The body defines first and second openings communicating with the interior space adjacent to, and preferably at, the ends of the interior space. A first closure member is mounted to the body for movement between an open position in which the first closure member does not fully close the first opening and a closed position in which the first closure member fully closes the first position, the first closure member being selectively movable from said open position to said closed position. Likewise, a second closure member is mounted to the body for selective movement from an open position in which the second closure member does not fully occlude the second opening and a closed position in which the second closure member fully occludes the second opening.

Desirably, the body, the first closure member or both are arranged for connection to the exhaled breath stream so that the exhaled breath stream may be directed through the interior space or bore of the body. Most preferably, the first closure member is arranged to fit directly within the patient's mouth so that the patient can blow through the device by holding the first closure member in his or her mouth.

The device may be provided with latch means for latching the closure members in their closed positions upon movement of the closure members to their closed positions so that the sample is permanently trapped within the interior space or bore of the body when the closure members are advanced from their open positions to their closed positions. A selective access device such as a puncturable septum bounding the bore may be provided so as to permit the withdrawal of the captured sample from within the interior space for testing. In a particularly preferred arrangement, each closure member has a generally tubular cavity and an end wall extending across the cavity. The body is telescopically received in the tubular cavities of the closure members so that the body lies between the closure members. In the open positions the end walls of the closure members are remote from the body, but the end walls of the closure members are disposed adjacent to the body and abut the body when the closure members are advanced to their closed positions. One or both of the closure members may include a resilient member mounted on its end wall for sealingly engaging the body when the closure members are in their closed positions. The resilient member of at least one closure member may include a puncturable septum, the septum bounding the interior space or bore of the body when the closure member is in its closed position. Thus, the septum of the resilient member may serve as the aforementioned access means.

In the preferred arrangement discussed above and in other preferred arrangements, both closure members are mounted to the body so that the same can be moved from their open positions to their closed positions. Most preferably, the closure members are mounted to the body so that both closure members can be driven from their open positions to their closed positions in response to a single actuating movement by the user, such as a single displacement or rotation of one closure member relative to the other closure member. Thus, the closure members may be disposed on opposite sides of the body, with the body disposed therebetween, so that movement of the closure members towards one another will advance both closure members towards the body, from their open positions to their closed positions. Also, the closure members may be rotatably mounted to the body such that rotation of one closure member relative to the other will bring both closure members to their closed positions. Such an arrangement may include helical threads on the body and helical threads on both of the closure members. All of these helical threads may be of the same hand and, preferably, coaxial with one another. Thus, as one closure member is rotated, it will first rotate relative to the body and advance to its closed position, and then drive the body in rotation so as to rotate the body relative to the other closure member and bring the other closure member to its closed position.

Further aspects of the present invention include methods of capturing a sample of expired breath from a stream of breath. Preferred methods according to this aspect of the invention desirably include the step of directing a stream of expired breath through an interior space in a sampling device by passing the stream into the interior space through a first opening on one side of the interior space and out of the interior space through a second opening on the opposite side of the interior space, and then closing both openings thereby interrupting the stream of breath and trap a sample of the stream in the interior space. As in the devices discussed above, continuous passage of the stream of breath through the interior space provides excellent purging action, so that the trapped sample is truly representative of the breath at the time that openings are closed. Desirably, both openings are closed concomitantly with one another in a single action. The method most preferably further includes the step of transporting the trapped sample in the sampling device and then subsequently withdrawing a portion of the sample from the sampling device for analysis.

These and other objects, features and advantages of the present invention will be more readily apparent from the detailed description of the preferred embodiments set forth below, taken in conjunction with the accompanying drawings.

BRIEF DESCRIPTION OF THE DRAWINGS

In the drawings in which similar elements are given similar reference characters.

DETAILED DESCRIPTION OF THE PREFERRED EMBODIMENTS

Figure 3:
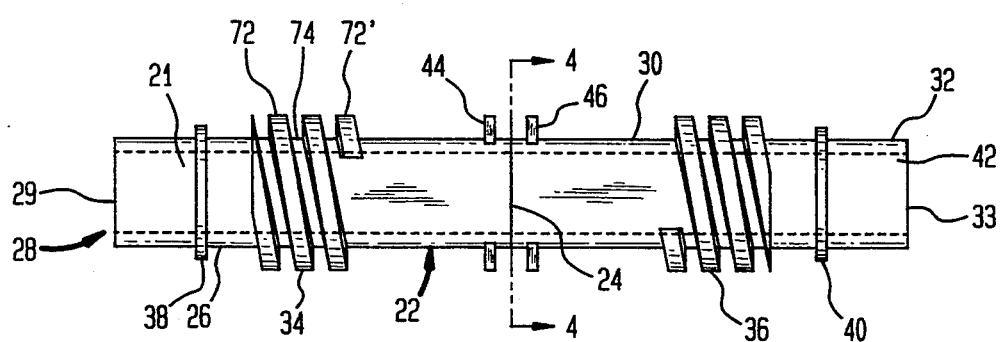
FIG. 3 is a side elevational view of the body member of the device of FIG. 1, partially cut away, to reveal an interior detail.

A device 20 in accordance with one embodiment of the invention includes an elongated hollow body member 22, best seen in FIG. 3, having a midplane 24, a first section 26 extending from midplane 24 to a first end 28 and a second section 30 extending from midplane 24 to a second end 32 with a bore 21 extending from first end 28 to second end 32. Bore 21 has a first opening 29 at end 28 and a second opening 33 at end 32. Bore 21 is substantially straight. The diameter or dimensions of bore 21 in directions transverse to its length is substantially smaller then the length of the bore. Desirably, the ratio of length to width of bore 21 is at least about 3:1, and more desirably at least about 5:1. Preferably, the width or diameter of bore 21 is between about 7 mm and about 20 mm, and more preferably between about 10 mm and about 15 mm.

A first external helical thread portion 34 is positioned approximately half-way between midplane 24 and first end 28. A second external helical thread portion 36 is positioned approximately half-way between midplane 24 and second end 32. Both of these threads are right-handed. A sealing ring 38 is spaced from first end 28 and extends completely around the exterior surface of first section 26. A similar sealing ring 40 extends completely around the exterior surface of second section 30. The interior edges of bore 21 at the first opening 29 and at second opening 33 are rounded to form closure seats 42.

Figure 4:
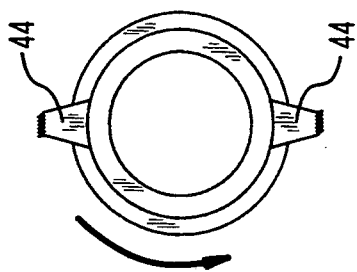
FIG. 4 is a front elevational view, in section, taken along the line 4—4 in FIG. 3.

Outwardly-extending ratchet projections 44 are formed integrally on the exterior surface of the first section 26 of body 22. As shown in FIG. 4, each projection 44 has unidirectional ratchet teeth 80 formed on its outermost tip. Teeth 80 have steep, generally radially-extensive faces 78 facing in the counterclockwise direction as viewed from the midplane 24, and gently-sloping faces 76 facing in the opposite, clockwise direction. Similar projections 46 are provided on the second part 30 of body 22. The teeth on projections 46 face in the opposite circumferential direction, i.e., with the steep faces of the teeth facing clockwise as seen from the first end 32 of body 22.

Figure 6:
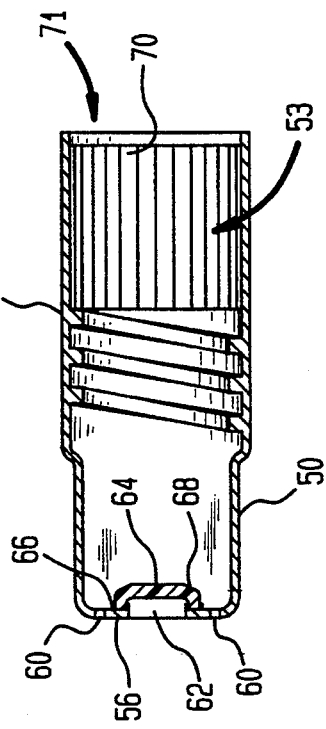
FIG. 6 is a side elevation, in section, of a closure member of the device as shown in FIG. 1.

Positioned upon body 22 are a first closure member or cap 50 which overlies first section 26 of body member 22 and a second closure member or cap 52 which overlies second section 30 of body member 22. As shown in FIG. 6, first closure member or cap 50 is a generally tubular member with a longitudinal cavity 53 therethrough of a diameter sufficiently large to permit the first cap 50 to be assembled over the first section 26 of the body member. An interior helical thread portion 54 in cavity 53 is complementary with first external threaded portion 34 of the body member to permit cap 50 to be advanced along body member 22 as desired.

Figure 7:
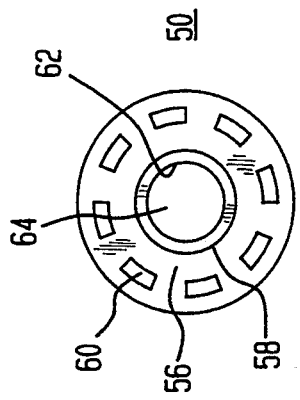
FIG. 7 is a front elevational view of a closure member of the device as shown in FIG. 1.

The closure member or cap also has an end wall 56. As best seen in FIG. 7, end wall 56 has a central section 58 with a hole 62 and a series of peripheral apertures 60 surrounding the central section 58 and hole 62. Apertures 60 and hole 62 extend entirely through end wall 56. An annular groove 66 is formed in the inner face of end wall 56 so that the annular groove surrounds the central hole 62 and lies between the central hole 62 and peripheral apertures 60. The closure member or cap 50 further has a set of unidirectional ratchet splines 70. Splines 70 have steep, substantially radically extensive surfaces facing in the counterclockwise direction as seen from the open end 71 of closure member or cap 50 and have relatively gently sloping surfaces facing in the opposite, clockwise direction. The shapes of splines 70 are generally complementary to the shapes of the splines 80 on projections 44 of the body member, so that these splines can be interengaged with one another.

An elastomeric, resilient sealing member 68 is mounted to the inner face of end wall 56. Sealing member 68 is seated in annular groove 66. The sealing member includes a puncturable septum 64 overlying central hole 62. Sealing member 68 terminates radially inwardly of the peripheral apertures 60 in the end wall 56 and hence does not obstruct these apertures.

A second cap or closure member 52 (FIG. 1) is generally similar to the first cap member 50. Thus, the second cap member has peripheral apertures 61 and a central aperture 63 in its end wall. A similar resilient elastomeric sealing member 69 overlies the central hole 63 and defines a puncturable septum in alignment with that central hole. The second cap or closure member 52 has an interior bore or cavity 55 with threads 57 complementary to threads 36 on the body, and further has splines 59 similar to the splines 70 of the first cap or closure member 50. However, the splines 59 of the second cap or closure member face in the opposite direction, i.e., so that the steep or radially extensive surfaces of the splines face in the clockwise direction as seen from the open end of closure member 52.

Figure 1:
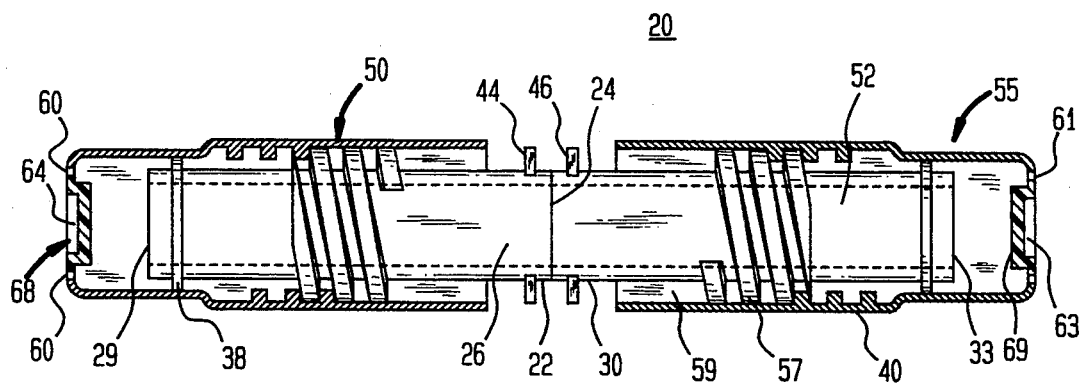
FIG. 1 is a further sectional view of a breath collection device constructed in accordance with one embodiment of the invention, shown in its open position.

The device is initially provided to the user in the condition illustrated in FIG. 1. In that condition, both closure members or caps 50 and 52 are in their respective open positions. In the open positions, the end walls of the caps or closure members are remote from the ends of body 22. Therefore, the sealing members 68 and 69 are remote from the open ends 29 and 33 of bore 21. The caps or closure members are of a relatively small external diameter, preferably less than about 25 mm. Therefore, the patient can place one cap in his or her mouth and exhale through the device. In the condition illustrated in FIG. 1, with both caps in their open position, the patient's breath can pass inwardly through the peripheral apertures 60 in first cap or closure member 50, through the first opening 29 at one end of the bore, through the bore 21 and out through the second opening 33 and through the peripheral opening 61 in the second cap or closure member 52. The sealing rings 38 and 40 substantially block passage of the breath sample through the annular spaces between the outside of the body and the inside of the caps or closure members. In this regard, it is not essential that the sealing rings 38 and 40 provide a perfect, airtight seal. Rather, the sealing rings need only assure that the bulk of the exhaled breath sample is directed through bore 21.

As exhalation proceeds, the air originally present within bore 21 is effectively purged therefrom. The breath flow through the bore is substantially unidirectional. There are no significant dead spaces or eddy-current inducing features inside the bore, so that the bore is effectively swept by the exhaled breath. Therefore, as exhalation proceeds further, the initial portions of the breath stream are effectively swept out of the bore by succeeding portions of the breath stream. At the desired time in the exhalation cycle, the patient (or a technician) twists first end cap or closure 50 in the clockwise direction relative to second closure or end cap 52. If the first end cap is engaged in the patient's mouth, this may be accomplished by turning the second end cap in the counterclockwise direction while leaving the first end cap stationary.

As the caps or closure members 50 and 52 turn relative to one another, one or both of the cap or closure members turns relative to the body, thereby advancing the threads on that cap along the body and bringing the end cap to a closed position. Thus, the first cap or closure member 50 is advanced to the closed position illustrated in FIG. 2, wherein the sealing member 68 bears on the body 22 and specifically on the seat at the first opening 29 of bore 21, thereby occluding the first opening. Likewise, the second closure member or cap 52 is advanced to its closed position. In that closed position, the end wall of the second closure member or cap is adjacent to the body, and the sealing member 69 carried on that end wall occludes the second opening 33 of bore 21.

Figure 2:
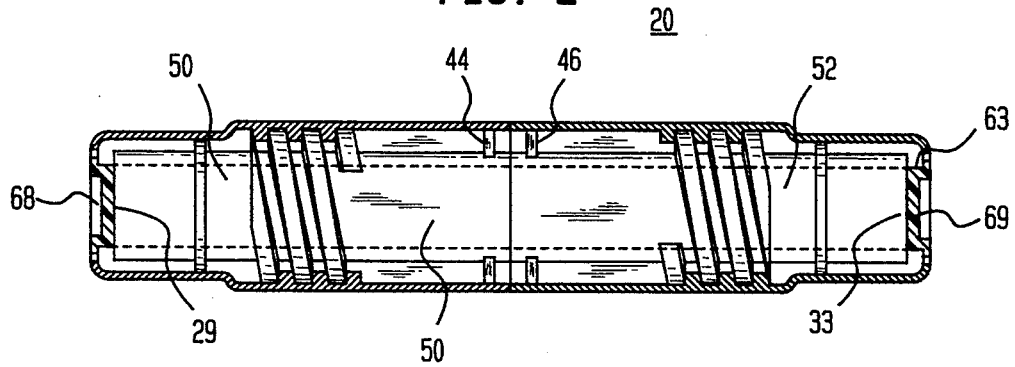
FIG. 2 is a side elevational view of the device of FIG. 1, shown in its closed position.

During the twisting motion, the end caps may advance towards their respective closed positions either simultaneously or sequentially in any order. However, once one end cap has been fully advanced to its closed position, with the associated sealing member bearing upon the body, that end cap cannot advance further. Therefore, any additional twisting motion of the end caps relative to one another will be taken up entirely by advancement of the remaining end cap, until both caps or closure members are fully advanced to the closed positions as illustrated in FIG. 2. Regardless of which cap or closure member moves first, both caps or closure members will be fully actuated from their open positions to their respective closed positions in response to the single turning or twisting movement of the end caps relative to one another.

Figure 5:
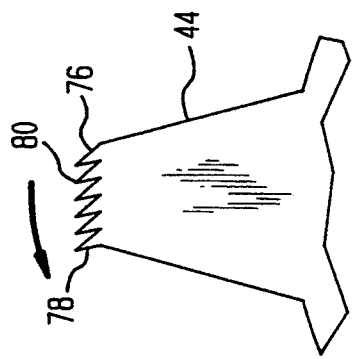
FIG. 5 is a greatly enlarged, fragmentary view of the detent structure of the base member of FIG. 3.

As first cap or closure member 50 is advanced to its closed position, the splines 70 on the interior surface of the cap or closure member pass over the splines 80 on projection 44. The gently sloping surfaces of the interior spline 71 ride over the gently sloping surfaces 76 on splines 80 as the cap or closure member rotates relative to the body in the advancing direction, indicating by the arrows in FIGS. 4 and 5. However, the cap or closure member 50 cannot rotate relative to the body in the opposite direction. The steep surfaces of splines 71 on the cap are engaged with the steep surfaces 78 of splines 80 on projections 44. Thus, once cap or closure member 50 has advanced to its closed position, it is latched in that position. Likewise, the second cap or closure member 52 is latched in its closed position by the interengagement of interior splines 59 and the splines on projection 46.

Thus, as soon as the patient or technician has executed the simple twisting motion required to bring the caps to the closed positions, a breath sample has been securely captured and sealed in bore 21. The device, with the trapped breath sample therein, can be transported and stored. In one common application, the breath sample is taken at a clinic or physician's office, and the device with the breath sample therein is transported to a laboratory for analysis. The septum 64 defined by sealing member 68 or the similar septum defined by sealing number 69 can be punctured by a conventional hypodermic needle to provide access to the sample. For example, a conventional syringe and needle may be used to withdraw some or all of the sample from within the bore. Once the needle is withdrawn, the septum seals itself so that no portion of the sample can escape and no external gases or the like can enter the device 20. Septa 64 can be placed in only one cap or both caps if desired.

The device 20 allows breath samples to be retained for periods of time long enough to permit transport to an analytical laboratory without substantial loss or contamination by atmospheric gases. Preferably, the body and closure members are molded from a polymer which provides a barrier against diffusion of gases which are significant in the analysis to be performed. Merely, by way of example, impact-modified acrylonitrile-methyl acrylate copolymer provides a satisfactory barrier against diffusion of carbon dioxide and oxygen. Resilient members 68 and 69 should also be selected to provide satisfactory diffusion resistance. Butyl rubber or bromobutyl rubber provides satisfactory resistance to diffusion of carbon dioxide. Other polymers can be used to block diffusion of other gases. If desired, the parts can be formed from multiple layers incorporating plural polymers provided with so-called "barrier coatings" of the types used on polymeric packaging to provide additional diffusion resistance. Non-polymeric materials such as metals, glass and ceramics may also be used. A desiccant may be placed in bore 21 to remove water vapor from the sample.

Figure 8:
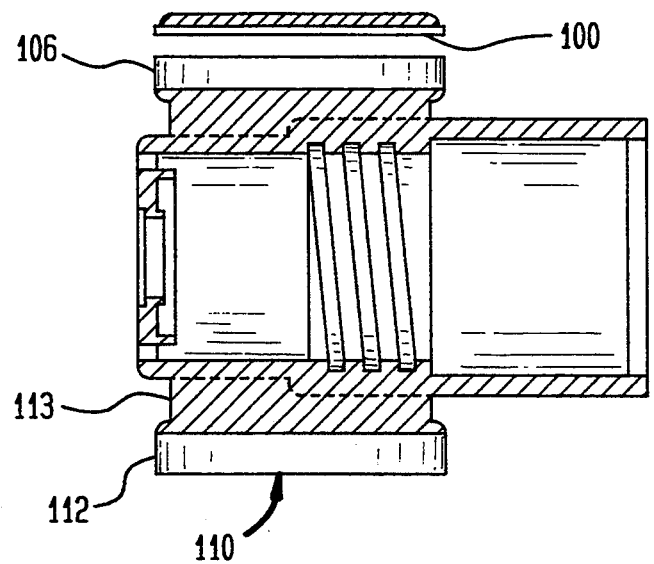
FIG. 8 is a sectional view of a component used in a device according to a further embodiment of the invention.
Figure 9:
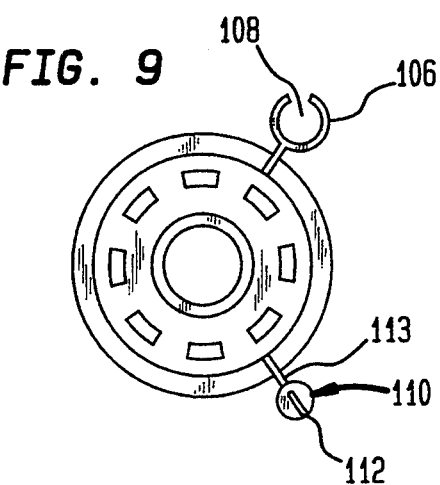
FIG. 9 is an end elevational view depicting the component of FIG. 8.

In an alternate arrangement, partially illustrated in FIGS. 8 and 9, one end cap or closure member 100 of a device as discussed above may be provided with interlockable elements so that a plurality of sampling devices can be fastened together after sample acquisition. In this arrangement, the second end cap 100 of each sampling device includes an integrally molded partial loop fastener 106 having a slot 108. The end cap further includes a rod 110 having a slot 112 formed therein. Rod 110 is connected to the main portion of the end cap by a web 113. In use, after samples have been captured in several sampling devices, the rod 112 of one sampling device can be inserted into the partial loop fastener 106 of another sampling device to fasten the sampling devices together. These elements can be securely interengaged with one another inasmuch as rod 110 can be compressed slightly due to the presence of slot 112 and loop fastener 106 can expand slightly. Web 113 on one device is received in the slot 108 of the attached device.

Such attachment can be used where several samples are taken from the same patient and the samples are to be maintained together for transport to a clinical laboratory. For example, in some diagnostic tests involving administration of drug or test reagent, it is desirable to obtain a so-called "baseline" sample before administration of the drug or reagent, and to then obtain samples at predetermined intervals after administration. The attachment devices on the cap or closure members of the sample device materially aid in keeping the various samples from a single patient together and in the proper order. Desirably, only one cap or closure member on each sample device is provided with the attachment devices, so that the other cap or closure member, without such devices, can be readily received in the patient's mouth for use as described above. Other devices for attaching plural sampling devices to one another, such as separately formed clips, fasteners, bandoliers, trays and packages can also be used.

Figure 10:
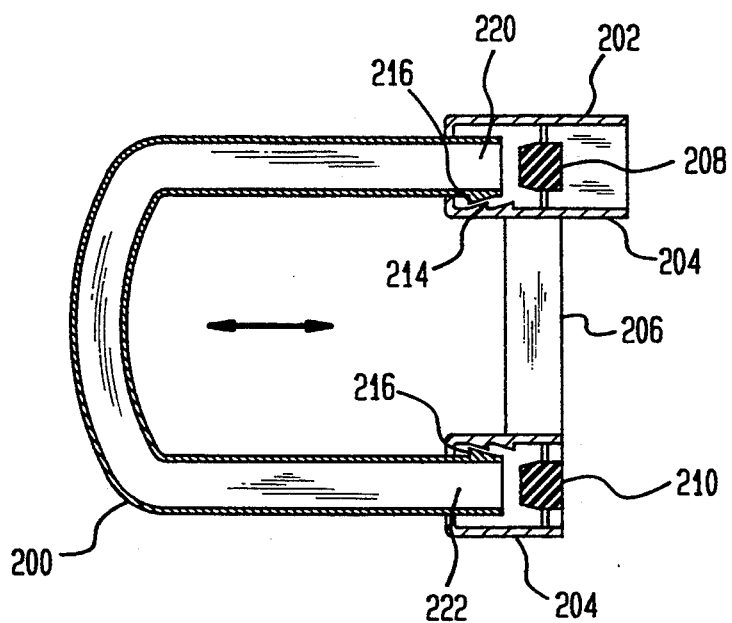
FIG. 10 is a diagrammatic sectional view depicting a device in accordance with a further embodiment of the invention.

Numerous other embodiments of the present invention can be employed. For example, as illustrated in FIG. 10, the body 200 of the device may be constructed as a generally U-shaped tube, and the caps or closure members 202 and 204 may be fastened together, as by a bar 206, to form a single integral unit. Closure member 202 may be provided with an extension 204 to serve as a mouthpiece, and the closure members may be provided with resilient sealing elements 208 and 210 similar to the resilient elements discussed above. The closure members may be provided with teeth 214 for engaging ratchet teeth 216 on the body 200.

In operation, the closure members are initially positioned as illustrated in FIG. 10, with the resilient sealing elements 208 and 210 remote from the ends 220 and 222 of the U-shaped tube or body 200. The patient takes mouthpiece 204 in his or her mouth and blows through the device, thus purging the interior space within tube 200. In this regard, even though tube 200 is not straight, it is effectively an elongated, continuous flow path, so that the breath forced through the tube by the patient is directed in substantially unidirectional flow along the length of the tube, from end 202 and 222. At the appropriate time, the closure members or end caps and the sealing elements are moved relative to the tube by moving the bar 206 and tube 200 towards one another as indicated by the arrows in FIG. 10, thereby forcing the sealing elements 208 and 210 into engagement with the ends 220 and 222 of the tube and sealing both ends substantially simultaneously. The sealing elements are locked into their closed positions by the interengagement of ratchet teeth 214 and 216. Here again, sealing elements 208 and 210 desirably include puncturable septa to permit due withdrawal of the sample.

Figure 11:
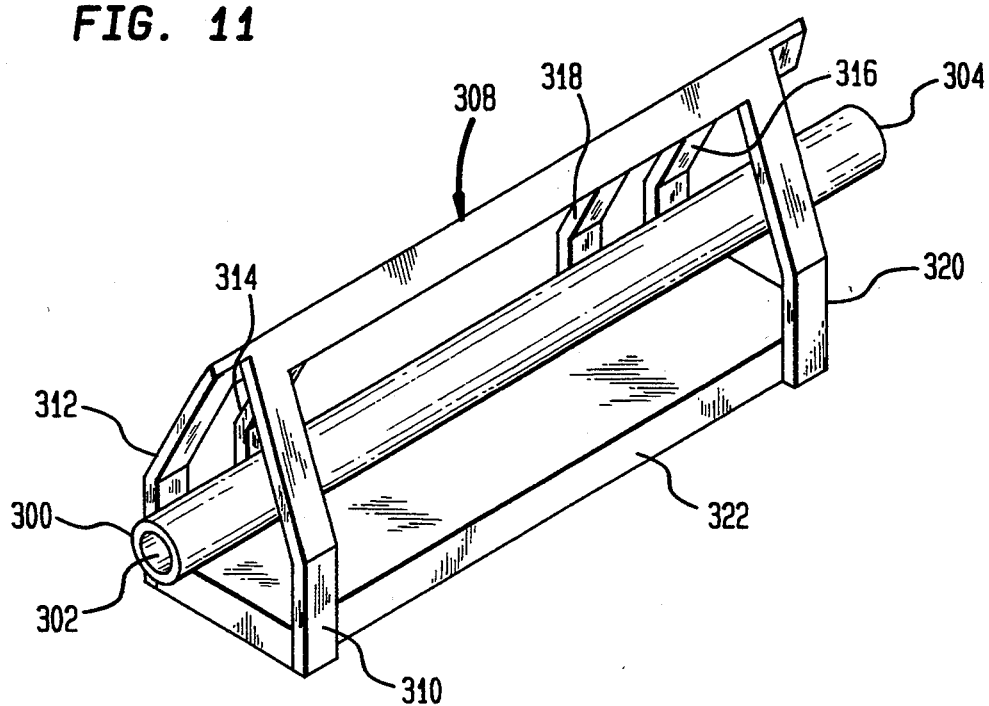
FIG. 11 is a diagrammatic perspective view depicting a device in accordance with yet another embodiment.

As illustrated in FIG. 11, devices other than movable closure elements may be used to close the ends of the interior space or bore, and thereby block communication with the openings. Thus, the sampling device incorporated in FIG. 11 includes a continuous flexible tube 300 having a first open end 302 and a second open end 304. The tube is loosely held inside of a spring clip 308. Spring clip 308 has an arm 310 extending to one side of tube 300 adjacent first end 302 and a pair of opposed arms 312 and 314 extending to the opposite side of tube 300, also adjacent first end 302. First arm 310 is aligned with a gap between opposed arms 312 and 314. Likewise, an arm 320 and a pair of opposed arms 316 and 318 are disposed on opposite sides of tube 300 adjacent the second end 304 of the tube. In the disengaged position shown, the arms are under tension due to the resilience of the clip itself, such that the arms tend to swing towards one another. The arms are held away from one another by a blocking element 322 disposed between the ends of the arms. In use, the patient can direct a breath sample through the tube, from first end 302 to second end 304, thus purging the interior of the tube. At the appropriate time, blocking element 322 is pulled out of the spring clip, thus allowing arm 310 and arms 312 and 314 to swing towards one another to pinch tube 302 shut adjacent first end 302. At the same time, arm 320 and arms 316 and 318 swing together, thereby pinching the tube shut adjacent the opposite second end 304. Thus, the breath sample is trapped within the tube, within the areas closed by the pinching arms. The tube wall itself provides a puncturable septum for subsequent access to the sample.

Numerous additional variations and combinations can be employed. For example, movable closure elements such as used in FIGS. 1–10 can be actuated by means other than screw threads or sliding movement. Mechanical devices such as toggles, cams, ramps and the like can be used to move the closure elements. The closure element at the first or inlet end of the interior space may be a check valve element biased to a closed position by a separately formed spring or by its own resilience, and momentarily held in the open position by the force of the patient's breath. Movable valve elements can be actuated by electrical, pneumatic or similar devices either included in the sampling device or external to the sampling device. For example, the sampling device can be mounted in a holder and the holder can be provided with solenoid-actuated or pneumatically-actuated plungers to force the valve elements closed in response to an externally applied signal.

The pinchable closures illustrated in FIG. 11 can be applied to a device wherein the remainder of the body or interior space defining element is rigid. Thus, sections of pinchable tube can be mounted adjacent the open ends of such a body. In a further variant, the pinchable tubes can be replaced by other sealable closures such as, for example, closure members bearing pressure sensitive adhesives or thermoplastic tubing adapted to be heat-sealed by an external device. These and other ways of closing communication from the interior space to the openings can be employed.

In the devices discussed above, the interior space or volume within the body is an elongated bore having a length along its lengthwise or end to end direction substantially greater than the diameter or transverse dimensions of the bore, and having a substantially uniform diameter or transverse dimension from end to end. Such an arrangement generally provides efficient purging. As discussed above with reference to FIG. 10, it is not essential that the bore be straight. Merely by way of example, the bore may be formed in a spiral, S-curve or other configuration. Also, the interior space or volume may be of a non-uniform diameter. If desired, interior baffles or structures can be provided to facilitate purging of the interior space by the breath sample.

As numerous other variations and combinations of the preferred embodiment can be utilized without departing from the present invention, the foregoing description of the preferred embodiments should be taken by way of illustration rather than by way of limitation of the invention.

What is claimed is:

1. A device to segregate and retain a sample of expired breath from a stream of breath comprising:
   (a) a body defining an interior space having first and second ends and first and second openings adjacent said ends;
   (b) a first closure member mounted to said body for movement from an open position wherein the first closure member does not fully occlude the first opening to a closed position wherein the first closure member occludes the first opening; and
   (c) a second closure member mounted to said body for movement from an open position wherein the second closure member does not fully occlude the second opening to a closed position wherein the second closure member occludes the second opening,
   at least one of said body and said closure members being adapted to direct a stream of breath exhaled by a patient into said interior space by way of one said opening whereby a sample of expired breath may be captured in said interior space by directing the stream of breath through the interior space while both said closure members are in their open positions and moving both closure members to their closed positions, the device further comprising latch means for latching said closure members in their closed positions upon movement of said closure members to said closed positions.

2. A device to segregate and retain a sample of expired breath from a stream of breath comprising:
   (a) a body defining an interior space having first and second ends and first and second openings adjacent said ends;
   (b) a first closure member mounted to said body for movement from an open position wherein the first closure member does not fully occlude the first opening to a closed position wherein the first closure member occludes the first opening; and
   (c) a second closure member mounted to said body for movement from an open position wherein the second closure member does not fully occlude the second opening to a closed position wherein the second closure member occludes the second opening,
   at least one of said body and said closure members being adapted to direct a stream of breath exhaled by a patient into said interior space by way of one said opening whereby a sample of expired breath may be captured in said interior space by directing the stream of breath through the interior space while both said closure members are in their open positions and moving both closure members to their closed positions, the device further comprising means for mounting both of said closure members to said body so that both closure members can be moved from their open positions to their closed positions responsive to a single manually applied actuation movement of one said closure member relative to the other said closure member.

3. A device as claimed in claim 2 wherein said closure members are mounted to said body on opposite sides thereof so that movement of said closure members towards one another will advance both closure members from their open positions to their closed positions.

4. A device as claimed in claim 2 wherein said closure members are rotatably mounted to said body so that rotation of one said closure member relative to the other said closure member in a preselected rotation direction will cause rotation of both said closure members relative to said body and move both closure members from their open positions to their closed positions.

5. A device as claimed in claim 4 wherein said body defines a pair of helical body threads having parallel axes and said closure members have helical closure member threads engaged with said helical body threads.

6. A device as claimed in claim 5 wherein said helical body threads are coaxial with one another and of the same hand, said helical closure member threads being coaxial with said helical body threads and of the same hand as said helical body threads.

7. The device as claimed in claim 2 further comprising a puncturable septum bounding said interior space whereby a breath sample may be withdrawn from within said interior space by puncturing said septum.

8. A device as claimed in claim 7 wherein said septum is carried on one of said closure members.

9. A device to segregate and retain a sample of expired breath from a stream of breath comprising:
   (a) a body defining an interior space having first and second ends and first and second openings adjacent said ends;
   (b) a first closure member mounted to said-body for movement from an open position wherein the first closure member does not fully occlude the first opening to a closed position wherein the first closure member occludes the first opening; and
   (c) a second closure member mounted to said body for movement from an open position wherein the second closure member does not fully occlude the second opening to a closed position wherein the second closure member occludes the second opening,
   at least one of said body and said closure members being adapted to direct a stream of breath exhaled by a patient into said interior space by way of one said opening whereby a sample of expired breath may be captured in said interior space by directing the stream of breath through the interior space while both said closure members are in their open positions and moving both closure members to their closed positions, each said closure member having a generally tubular cavity and an end wall extending across said cavity, said body being telescopically received in said tubular cavities of said closure members, said end walls of said closure members being remote from said body when said closure members are in said open positions, said end walls of said closure member's being adjacent said body when said closure members are in said closed positions.

10. A device as claimed in claim 9 wherein each said closure member has a resilient member mounted on its end wall, said resilient members sealingly engaging said body when said closure members are in said closed positions.

11. A device as claimed in claim 10 wherein said resilient member on at least one said closure member includes a puncturable septum said septum bounding said interior space when such closure member is in its closed position, whereby a sample of breath captured in said interior space may be withdrawn from said interior space by puncturing said septum.

12. A device to segregate and retain a sample of expired breath from a stream of breath comprising:

(a) body means for defining an interior space and first and second openings on opposite sides of said interior space;

(b) inlet means for admitting breath to said interior space through said first opening, whereby a stream of breath may be directed through said interior space and out of said interior space through said second opening;

(c) valve means for closing both of said openings to thereby interrupt said stream of breath and trap a sample of said stream in said interior space; and (d) access means for providing access to said interior space to permit withdrawal of said trapped sample said valve means being initially arranged in an open condition such that both said openings are open, said valve means being selectively movable to a closed condition wherein both of said openings are closed.

13. A device as claimed in claim 12 wherein said valve means includes means for closing both of said openings in response to a single actuating movement.

14. A device as claimed in claim 12 further comprising latch means for retaining said valve means in said closed condition.

15. A device as claimed in claim 12 wherein said interior space has a pair of opposed ends, said first and second openings being adjacent said ends, said interior space generally in the form of an elongated bore having a dimension between said ends, along the length of the bore substantially greater than the dimensions of said bore transverse to the length.

16. A device as claimed in claim 15 wherein said bore is substantially straight.

17. A method as claimed in claim 18 further comprising the steps of transporting said trapped sample in said sampling device and then withdrawing a portion of the sample from said sampling device.

18. A method of capturing a sample of expired breath from a stream of breath comprising:

(a) providing a sampling device an interior space having first and second sides, a first opening on said first side of the interior space, a second opening on the said second side of said interior space, said sampling device also having first valve means for closing said first opening and second valve means for closing said second opening, said providing step being performed so as to provide said sampling device with said first and second valve means in an open condition such that said first and second openings are open; and (b) directing the stream of expired breath through said interior space in said sampling device by passing the stream into the space through said first opening on said first side of the interior space and out of said interior space through said second opening on said second side of said interior space; and (c) closing both of said openings by manually activating said first and second valve means substantially simultaneously to a closed condition to thereby interrupt said stream of breath and trap a sample of said stream in said interior space.

* * * * *

UNITED STATES PATENT AND TRADEMARK OFFICE
CERTIFICATE OF CORRECTION

PATENT NO. : 5,361,772
DATED : November 8, 1994
INVENTOR(S) : Murnick et al

It is certified that error appears in the above-identified patent and that said Letters Patent is hereby corrected as shown below:

Column 1, line 23 after the words "Stream at" delete the comma (,).
Column 12, line 25, change "said-body" to read -- said body --.
Column 14, line 9, after the word "device" insert the word --having--.

Signed and Sealed this

Seventh Day of March, 1995

Attest:

BRUCE LEHMAN

Attesting Officer

Commissioner of Patents and Trademarks